United States Patent [19]

Schwartz

[11] 4,450,574

[45] May 22, 1984

[54] CONTROL CIRCUIT FOR LIQUID CHROMATOGRAPH

[75] Inventor: Arnold Schwartz, Bridgeport, Conn.

[73] Assignee: The Perkin-Elmer Corporation, Norwalk, Conn.

[21] Appl. No.: 343,805

[22] Filed: Jan. 29, 1982

[51] Int. Cl.³ ............................................. G06F 15/46
[52] U.S. Cl. ......................................... 377/2; 377/27; 364/502
[58] Field of Search ........................ 377/2, 27, 39, 44; 364/502

[56] References Cited

U.S. PATENT DOCUMENTS 3,154,670 10/1964 Gossel ..................................... 377/2
3,604,903 9/1971 Hill et al. ............................... 377/2
4,063,077 12/1977 Wright ................................ 364/502

Primary Examiner—John S. Heyman
Assistant Examiner—N. Biase
Attorney, Agent, or Firm—Robert A. Hays; Edwin T. Grimes; Francis L. Masselle

[57] ABSTRACT

A circuit for controlling the proportions of a plurality of solvents being introduced into a column of a liquid chromatograph. The circuit compensates for the compressibility of liquids by dividing the time during each pumping cycle during which the pump is delivering liquid to the column into a known number of intervals. A circuit responsive to the interval signals opens and closes solvent valves thereby allowing the solvents to be introduced into the pump in the desired proportions.

24 Claims, 11 Drawing Figures

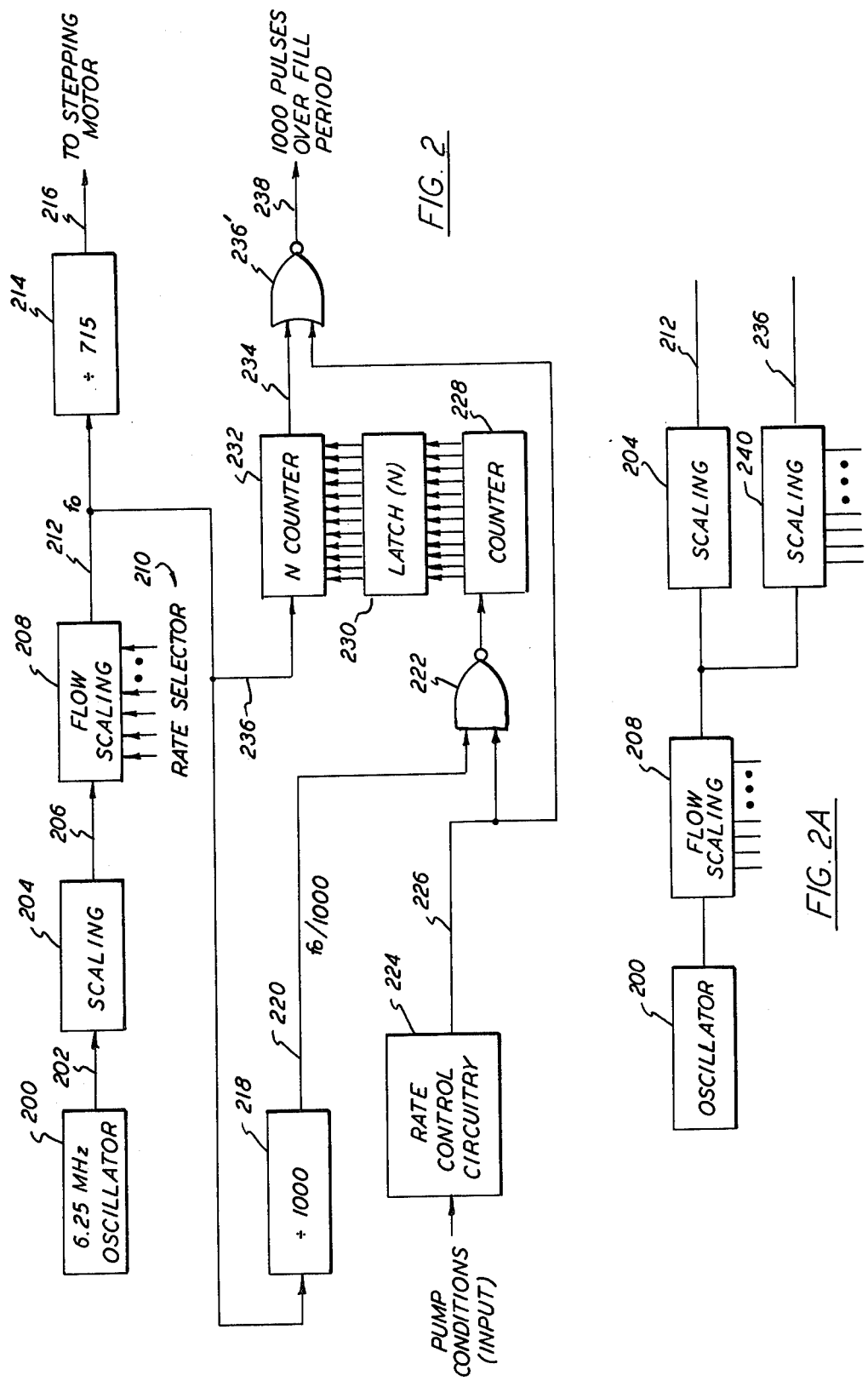

| FIG. 3A | FIG. 3B |

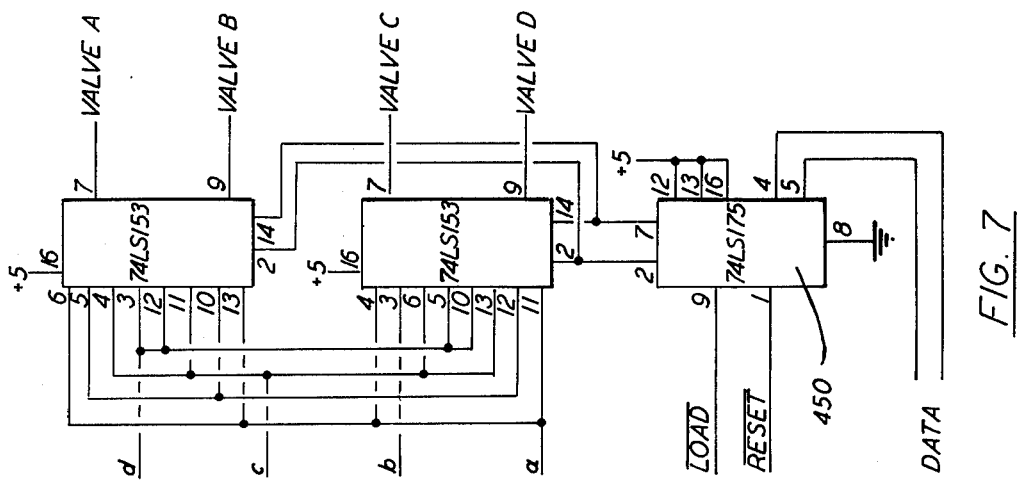
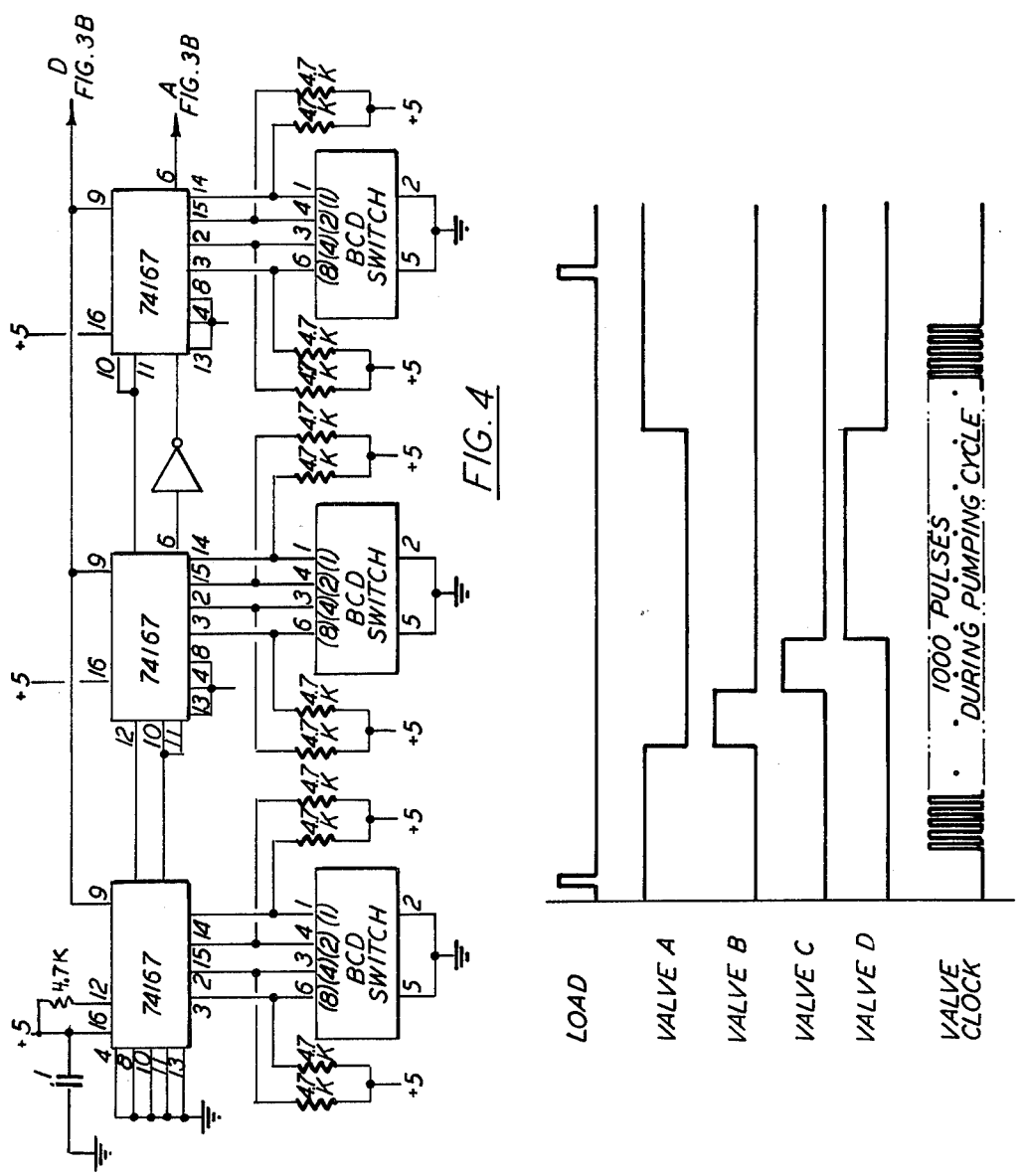

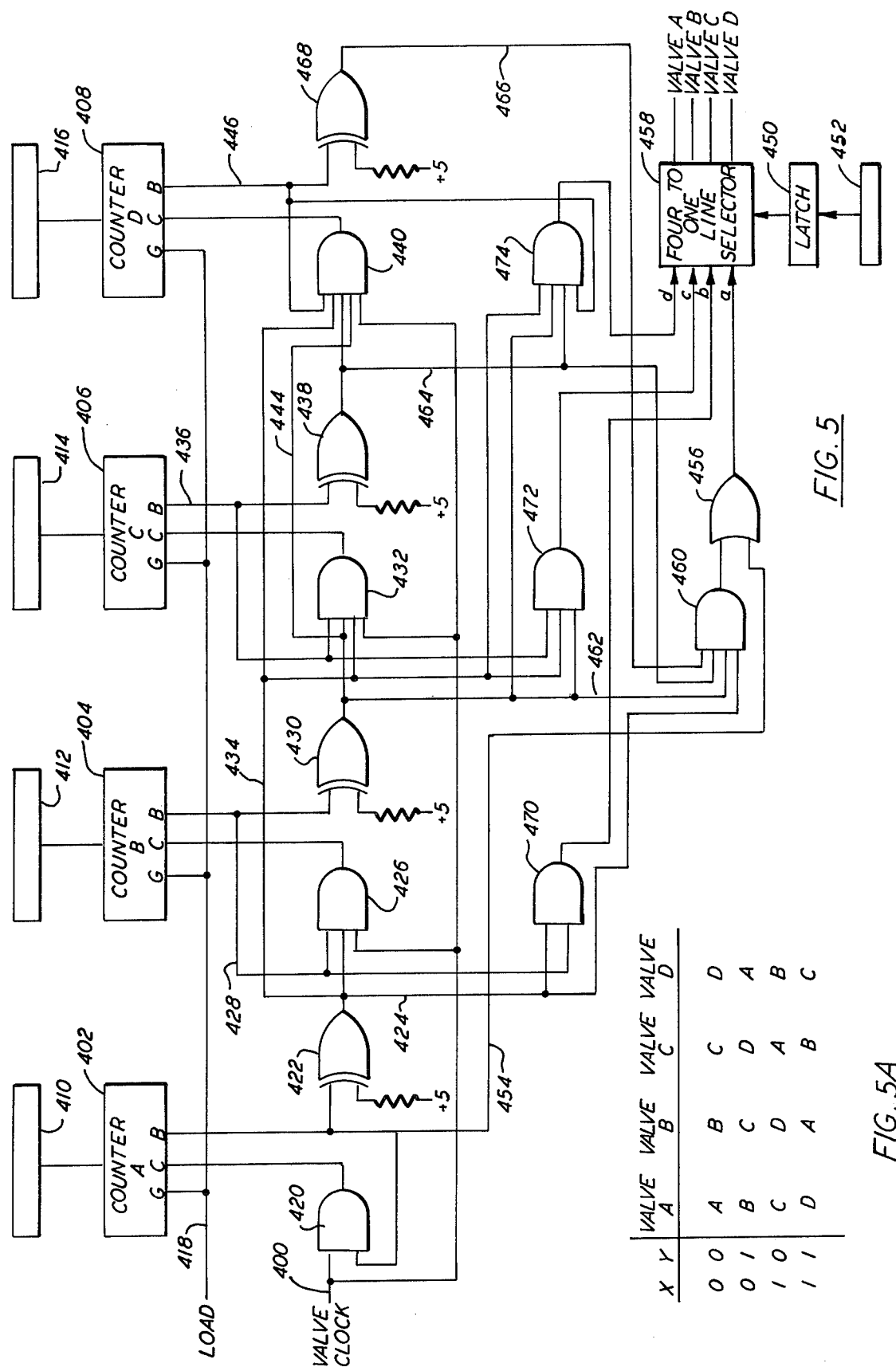

CONTROL CIRCUIT FOR LIQUID CHROMATOGRAPH

The present invention relates broadly to the field of liquid chromatography and particularly to a control circuit useful in assuring that liquid mixtures are introduced into the chromatograph column in the proper proportions.

In the field of liquid chromatography, an unknown substance is introduced along with a solvent solution into a column. The solvent solution is usually comprised of one or more liquids which are mixed together in known proportions. However, during testing of a particular sample, it is desirable to change the proportions of the individual liquids which comprise the solvent solution into which the sample is introduced. In this manner, the researcher can learn more characteristics of the sample being tested.

In some liquid chromatographs utilized to date, the sample and its solvent carrier is prepared and introduced into the column in various ways. Typically, there are one or more pumps powered by one or more motors. Solvents are introduced into the pump according to the desired constituent mix. The individual solvents are then introduced into a mixer and thereafter are introduced through a pulse damper into the instrument column.

Systems of the type generally described above, however, do have some inherent design problems, especially where the systems are of the type where the solvent composition is changed from one injection into the column to another. The column filling pump introduces a volume of solvent into the column into which some unknown sample has been introduced. The volume of the solvent which is introduced into the column, however, is not known exactly. This imprecision is caused by the fact that fluids are somewhat compressible and that the compressibility varies from one liquid to another. As the fluid is delivered to the column by the delivery pump, the fluid is compressed as the pumping pressure goes up. Once the column back pressure is exceeded, the fluid in the pump is introduced into the column, but the volume of fluid introduced is not known exactly. This problem becomes even more acute in systems operating at high column pressures.

The prior art systems also have difficulty in connection with preparing the solvent mixture prior to its being introduced into the column. In typical systems, the pump fill cycle is not linear. That is, the rate at which the pump fills is not constant over the pump fill cycle. Accordingly, proportioning of solvents prior to being inserted into the column is difficult and frequently involves a table look-up technique to proportion the solvents. The apparatus for performing such a table look-up, however, is costly, as well as being more complicated than is desirable.

It is, therefore, a primary object of the present invention to provide a pumping control circuit useful in liquid chromatography to accurately proportion a plurality of solvents.

It is still a further objective of the present invention to provide a pumping control circuit which compensates for the compressibility of liquid being introduced into the column.

It is yet a further objective of the invention to provide a pump control circuit which maintains the proportion for each solvent.

It is a further objective of the present invention to provide a pump control circuit that does not require a table look-up for proper proportioning of solvents.

In achieving the foregoing and other objectives of the present invention, the control circuit is utilized in connection with proportioning a plurality of solvents to be pumped into the column of a liquid chromatograph. The proportioning valves are coupled between the solvent sources and a metering pump whose piston is coupled to the piston of a delivery pump. During the fill stroke of the metering pump, it is filled with a desired proportion of solvents. At the same time, the delivery pump is pumping fluid into the chromatograph column. During the return stroke of the metering piston, the content of the metering pump is transferred to the delivery pump. The amount transferred between the two pumps is identical to the volume of fluid delivered by the delivery pump during the preceding pumping cycle.

The control circuit of the present invention responds to clock pulses which are utilized for stepping a stepping motor used to drive the metering and delivery pistons. The control circuit in addition responds to a signal which indicates when the delivery piston has reached sufficient pressure to cause the fluid in the delivery pump to be pumped into the instrument column. The control circuit also responds to a signal indicating when fluid stops being pumped by the delivery pump. The circuit utilizes these signals to develop a stream of pulses at its output having, in the preferred embodiment, 1000 pulses produced in the same time as utilized by the delivery piston to actually pump liquid from the delivery pump to the column, i.e. the time during which the delivery pump pressure exceeds the column back pressure. The proportioning circuitry uses these 1000 pulses in controlling the time that the proportioning valves are open so that the solvents are introduced in the proper amount during the metering pump fill cycle.

BRIEF DESCRIPTION OF THE DRAWINGS

The foregoing and other objects, advantages and features of the present invention are described below in connection with the drawings illustrating a preferred embodiment of the present invention wherein:

FIG. 2 is a block diagram of the control circuit according to the present invention;

FIG. 2A shows a modification to the block diagram of FIG. 2;

FIG. 4 shows the manner in which the circuit of FIGS. 3A and 3B is modified to implement the modification of FIG. 2A;

FIG. 5 illustrates a circuit for utilizing the pulse stream produced by the circuitry of FIGS. 3A and 3B for controlling the solvent valves of FIG. 1;

FIG. 5A is a truth table governing the operation of the four to one line selector of FIG. 5;

FIG. 6 illustrates schematically the timing for opening and closing the valves of FIG. 1 by the circuitry of FIG. 5; and FIG. 7 illustrates one embodiment of a four to one line selector found in FIG. 5.

DETAILED DESCRIPTION OF THE INVENTION

Figures 1, 1A:
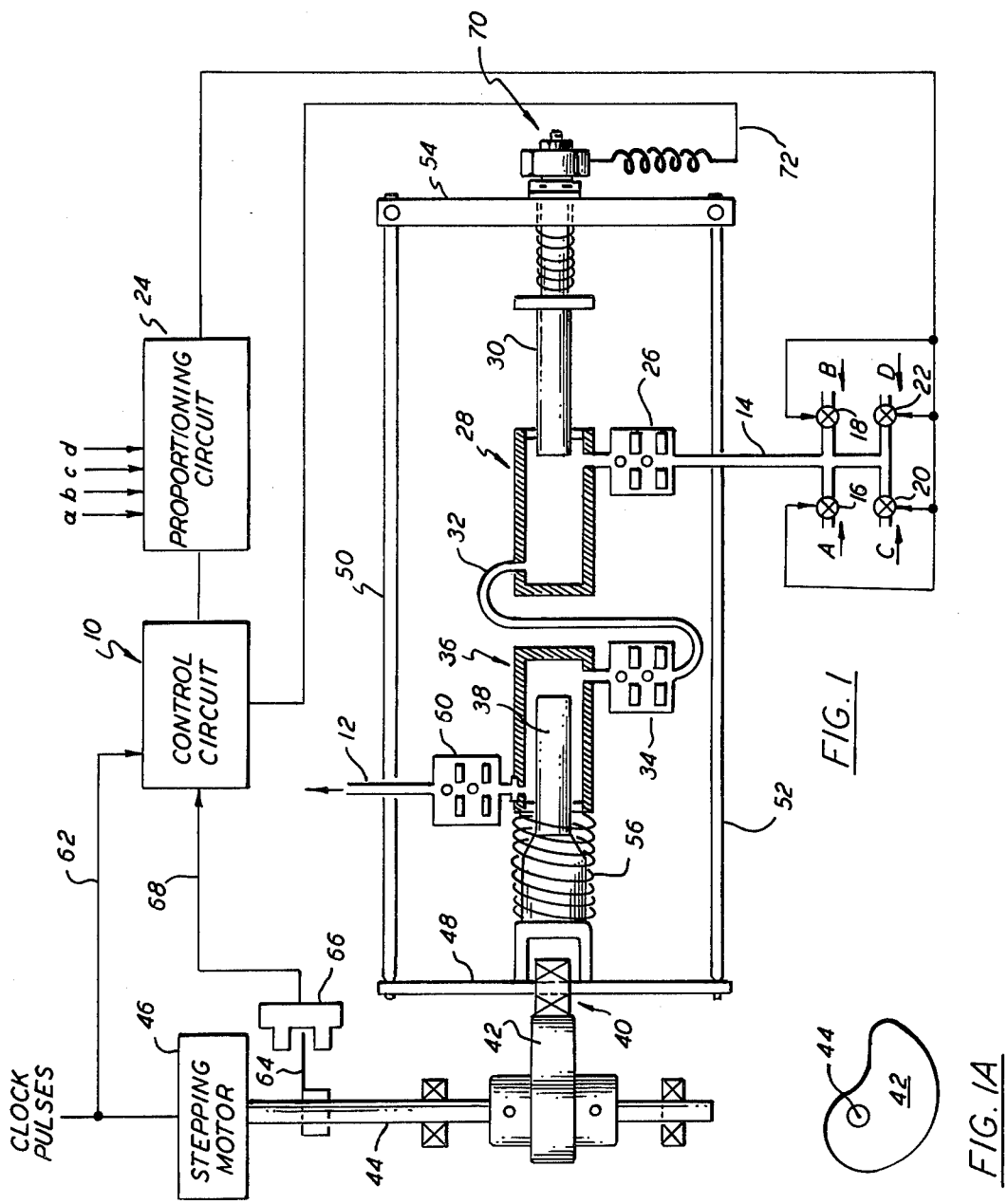
FIG. 1 is a schematic diagram of the pump configuration of a liquid chromatograph utilizing the control circuit of the present invention.
FIG. 1A shows the cam profile for the cam utilized in the configuration of FIG. 1.

FIG. 1 illustrates the operating environment in which the control circuit 10 of the present invention finds application. The objective of the configuration of FIG. 1 is to mix in the proper proportions the liquids A, B, C and D and deliver that proportioned liquid into a delivery pipe 12 which couples to the inlet of a column of a liquid chromatograph (not shown). The liquids A, B, C and D are respectively introduced into a delivery pipe 14 whenever the proportioning valves 16, 18, 20 or 22, respectively, are open. These proportioning valves 16, 18, 20 and 22 are controlled by a proportioning circuit 24 which has inputs labelled a, b, c and d, which indicate the desired percentage in the mixture each of the solvents A, B, C and D respectively, are to have.

The delivery pipe 14 couples between the proportioning valves 16, 18, 20 and 22 and a check valve 26 on the inlet side of a metering pump indicated generally at 28. Whenever the piston 30 of the metering pump 28 is moving in a direction toward the right, as viewed in FIG. 1, the metering pump 28 receives a liquid from the delivery pipe 14 via the check valve 26.

The outlet of the metering pump 28 is coupled by a transfer pipe 32 to a check valve 34 on the inlet side of a delivery pump 36. Whenever the piston 30 of the metering pump 28 is moving in a leftward direction, as illustrated in FIG. 1, fluid is transferred out of the metering pump 28 via the transfer pipe 32 and the check valve 34 and into the delivery pump 36.

The delivery pump 36 has a piston 38 which is connected to a cam follower 40, which itself is in contact with a cam 42. The cam 42 is mounted on a shaft 44 that is driven by a stepping motor 46. The cam follower 40 is mounted on a coupling shaft 48 which has coupled at opposite ends thereof to tie rods 50 and 52. The tie rods 50 and 52 have their opposite ends connected to a coupling rod 54, which in turn couples directly to the metering piston 30. Accordingly, whenever the stepping motor 36 causes the shaft 48 to turn, the cam 42 coupled thereto also turns. The coupling shaft 48 and the cam follower 40 are urged by a return spring 56 towards the left, as viewed in FIG. 1. As the cam 42 rotates, the cam follower 40 follows the circumference of the cam. The cam 42 preferably has a shape generally as illustrated in FIG. 1A, and, as the shaft 44 rotates, the cam follower 40 will move to the left and to the right to follow the surface of the cam 42. Whenever the delivery piston 38 moves in a leftward direction, this leftward motion is transmitted via the coupling shaft 48, the tie rods 50 and 52 and the coupling rod 54 to the metering piston 30, thereby causing it to move in a leftward direction as well. Likewise, when the piston 38 is driven in a rightward direction, the piston 30 is also driven in a rightward direction.

In accordance with the present invention, it has been found desirable to have the pump 28 contain a slightly larger volume of liquid than the pump 36. This is desirable because whenever liquid is transferred from the pump 28 to the pump 36 via the transfer pipe 32, the fluid from the pump 28 will completely fll the pump 36 as the volume transferred from pump 28 is slightly greater than that delivered by pump 36.

During the cycle when fluid is forced from the pump 36 through the check valve 60 and into the delivery pipe 12, the piston 38 is driven in a rightward direction by the cam 42 and the follower 40. At the same time, the metering pump 28 has its piston moving in a rightward direction thereby allowing it to be filled by the solvents A, B, C and D under control of the proportioning circuit 24, which in turn receives control information from the control circuit 10 and the proportioning inputs a, b, c and d.

The control circuit 10 is operative to develop a signal in response to signals developed from the pumping and electronics arrangement illustrated in FIG. 1 which corresponds to the time at which the pump 36 is at a pressure equal to or slightly in excess of the back pressure of the column. This time corresponds to the time at which fluid actually begins to be pumped from the pump 36 into the column. Because of the compressibility of liquids, this time will vary from one liquid to the next as a function of the compressibility of that liquid. The control circuit 10 is designed in accordance with the preferred embodiment of the present invention to divide the time period, during which the liquid is actually introduced into the column from the pump 36, into 1000 equal segments. These time segments are used in conjunction with the proportioning circuit 24 to control the proportioning valves 16, 18, 20 and 22 so that the proportions of the solvents A, B, C and D can be adjusted within 0.1 percent.

In order to develop these desired signals, the control circuit 10 is coupled by the line 62 to the clock or stepping pulse source for the stepping motor 46. In addition, the control circuit 10 responds to a shaft position sensor which includes a beam interrupter 64 affixed to the shaft 44 and a light source and sensor arrangement 66 which produces a signal on the line 68 indicating that the shaft 44 is in the position whereat the pump 36 can no longer deliver more fluid into the column via the delivery pipe 12. The interrupter 64 is affixed to the shaft 44 at the point where testing indicates the instrument is working correctly. The control circuit 10 also responds to a sensor 70, which is coupled to the piston 30. The sensor 70 produces a signal on the line 72 when the pressure in the delivery pump 36 exceeds the back pressure in the column so that fluid starts to flow from the pump to the column. The sensor 70 is described in greater detail in a copending patent application entitled "Solvent Delivery System" by Carl E. Schmid, which was filed on 1/29/82, U.S. patent application Ser. No. 343,807. The disclosure of that patent application is incorporated herein by reference.

Referring now to FIG. 2, which comprises a block diagram of one embodiment of the present invention, an oscillator 200 is provided for producing pulses on its output line 202 at a frequency, in the preferred embodiment, of 6.25 MHz. The frequency selected is not critical to the circuit operation but it must be selected to permit other system elements to operate in the desired range. The pulses on the line 202 are coupled to a scaling circuit 204 which modifies the frequency of pulses appearing at its output 206 to a desired rate which, in the preferred embodiment, is approximately 4.875 MHz.

The scaling selected is not critical to the circuit operation; however, the value for the scaling is selected so that the flow scaling circuit 208 can control the pump coupled thereto to deliver the desired flow rate of fluid into the column.

The pulses on line 206 are coupled to a flow scaling circuit 208, which is coupled to a flow rate selector 210. The selector 210 may comprise adjustable switches for controlling the scaling of the flow control 208. In the preferred embodiment, the rate selector 210 is set to a number between 1 and 99. The output of the flow control 210 is a pulse stream which, in the preferred embodiment, has a pulse rate varying between about 19 KHz and 1.9 MHz. These pulses on the line 212 are coupled to a divide by 715 circuit 214 which produces pulses at its output 216 at a rate which is desired to run the stepping motor used to drive the pump 28 and 36 of FIG. 1. The actual value by which the pulse rate at 212 is divided by circuit 214 is selected to match the particular stepping motor coupled thereto, as well as the pump coupled to the stepping motor so as to produce the desired pumping rate.

Those of skill in the art will recognize that the position of the scaling circuit 204 and the flow scaling circuit 208 can be interchanged without affecting the operation of the circuit of FIG. 2. Such a reversal is illustrated in FIG. 2A. This arrangement, in addition, includes a further pulse frequency scaler 240 whose output is coupled via line 236 to the counter 232 thereby replacing the pulses at $f_o$ on line 236, as illustrated in FIG. 2, with pulses at $Pf_o$ in FIG. 2A where P is a scaling factor. By adjusting the value of P, the circuit of FIG. 2A is made to operate correctly. This adjustment works in a manner similar to adjusting the position of the interrupter 64 in connection with the circuit of FIG. 2 to make the instrument work correctly.

The pulses on the line 212 are also coupled to a divide by 1000 circuit 218 which produces pulses on line 220 at a frequency equal to $f_0/1000$ where $f_0$ is the frequency of the pulses appearing on the line 212. The pulses on the line 220 are coupled to one input of a NAND gate 222 whose other input is coupled to the gate control circuitry 224. The gate control circuitry 224 responds to the pump conditions which indicate the start of the pumping cycle as well as the end of the pumping cycle. The output of the gate control circuitry 224 is placed onto line 226 so as to condition the NAND gate 222 to pass the pulses from line 220 into the first counter 228 only during the time period when the pump, as indicated by the gate control circuitry 224, is actually delivering fluid into the column.

After the conclusion of the pump cycle during which fluid is introduced into the column, the content (N) of the first counter 228 is transferred into a latch circuit 230. Then the counter 228 is reset so that during the subsequent pumping cycle, it can again count pulses from the line 220 during the period of time that fluid is being delivered by the pump to the column.

During the subsequent pumping cycle, the N counter circuit 232 is operational to produce a pulse at its output 234 for every N pulses being applied thereto via line 236. The pulses appearing on the line 234 are applied to one input of a second NAND gate 236'. The second input to this NAND gate 236' is the line 226 and, accordingly, the output 238 of the gate 236' comprises a plurality of pulses which occur over the time period defined by the gate control circuitry 224, which corresponds to the time during which the pump of FIG. 1 is actually filling the instrument column.

It will be understood by those of skill in the art that the circuit of FIG. 2 in fact produces 1000 pulses on line 238 during the time in which the pump of FIG. 1 is actually delivering fluid to the instrument column.

Figure 3A:
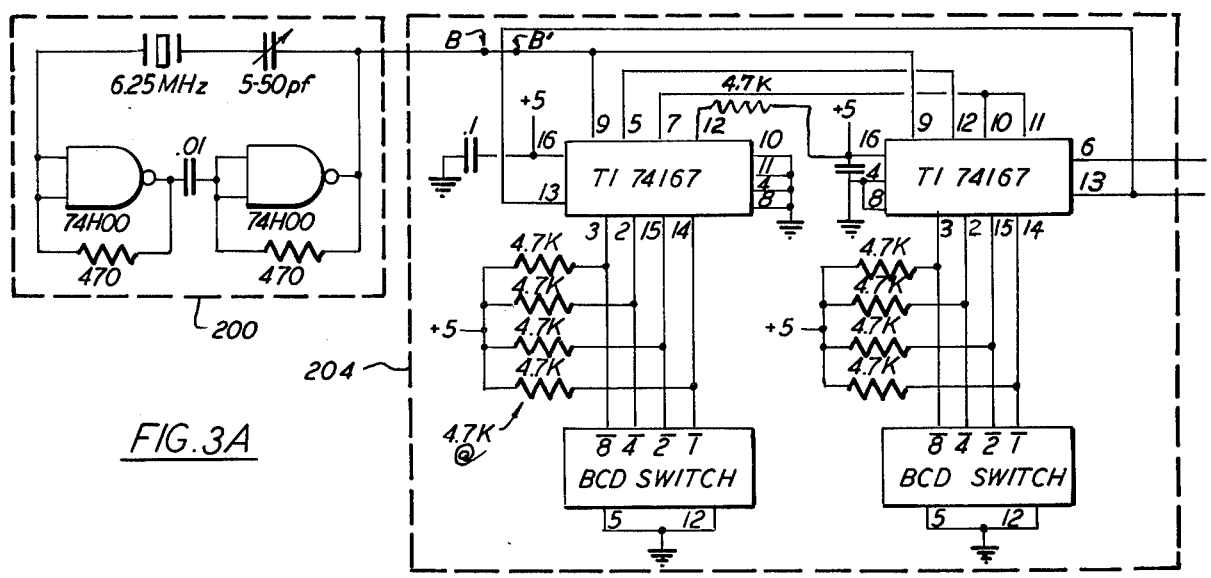
FIG. 3A and FIG. 3B comprise a detailed circuit diagram for the preferred embodiment of the present invention.
Figure 3:
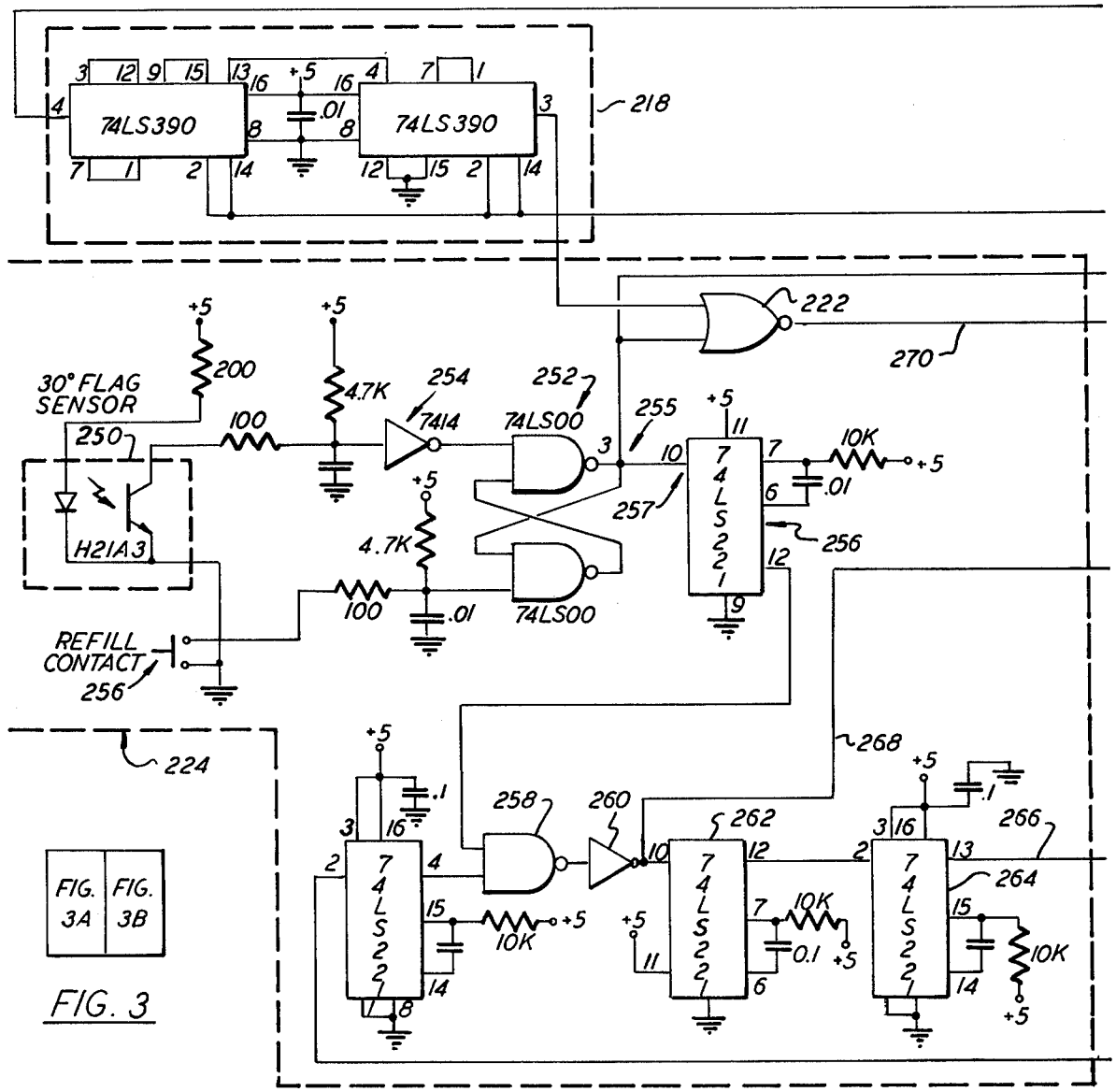
FIG. 3 illustrates how FIGS. 3A and 3B fit together.

Referring now to FIG. 3, a detailed circuit implementation for the block diagram in FIG. 2 is presented. It will be observed that in FIG. 3, as well as in other drawings in the present patent application, the circuit components are assigned a parameter value or standard commercial designation. This is done purely for clarity and reader convenience and is not intended as a limitation on component value or type, nor as a restriction on the scope of the invention.

The implementation of FIG. 3 is referenced by the numbered dotted lines to the block diagram of FIG. 2. The operation of the individual circuit types of the configuration shown in FIG. 3 will be well understood by those of skill in the art; however, for clarity, a few of the circuits will be hereinafter described in greater detail.

Within the gate control circuitry 24, a 30° flag sensor is illustrated generally at 250. This flag sensor comprises a light emitting diode and a photosensor, which are coupled into the circuit as illustrated. The flag sensor 250 is positioned as illustrated in FIG. 1 at 66 in a manner so a flag 64, mounted on the drive shaft 44 and turned by the motor 46, can interrupt a beam between the LED and the photo sensor portion of the flag sensor 250. In the preferred embodiment, the sensor 250 is a H21A3 manufactured by General Electric although other similar circuits might be used.

The flag sensor 250 is coupled to a flip-flop circuit 252 via an inverter 254 in a manner so that when the interrupter 64 on the shaft 44 interrupts the sensor 250 beam, the output of the inverter 254 is low, which sets the flip-flop 252 so its output of 255 is high. The flip-flop 252 output remains high until the refill contact, illustrated at 256, closes, which occurs when the pump 36 starts delivering fluid to the column. The switch 256 is opened where the rapid refill pump 28 begins to transfer fluid to the pump 36. The flip-flop 256 maintains a low level at 255 until the sensor 250 again detects the beam interrupter.

The flip-flop 252 couples via its output at 255 to a single shot circuit 256 configured to trigger on the rising edge of the pulse coupled to its input 257. The single shot 256 produces a pulse at its output which couples via a NAND gate 258 and an inverter 260 to a second single shot 262. This single shot 262 triggers on the rising edge of the pulse appearing at its input pin 10 to produce a pulse at its output which triggers yet another single shot 264. The pulse output by single shot 264 is coupled by line 266 to the first counter 228 which is reset thereby to all zero.

The output pulse of the inverter 260 is also coupled via the line 268 to the latch circuit 230. The pulse on line 268 causes the number in the counter 228 to be gated into the latch 230. Since the pulse occurs on line 268 before the pulse on line 266, each time a pumping cycle is complete, i.e., the pump 36 has pumped all the fluid it can into the column, the number of pulses counted by the counter 228 is transferred to the latch 230, and thereafter, the counter 230 is reset to zero. Thus, when the next pumping cycle begins, i.e., the pump 36 begins to deliver fluid to the column, the counter 228 will begin to count pulses occurring on line 270.

The clock pulses on line 270 are produced at the output of NOR gate 222, which is coupled to the output of the divide by one thousand circuit 218 and the flip-flop 252. Whenever both the inputs to the gate 222 are low, the output is high. Accordingly, the clock pulses from the divide by 1000 circuit 218 appears in inverted form on line 270 whenever the flip-flop 252 output at 255 is low, which occurs while fluid is being pumped into the column.

Figure 3B:
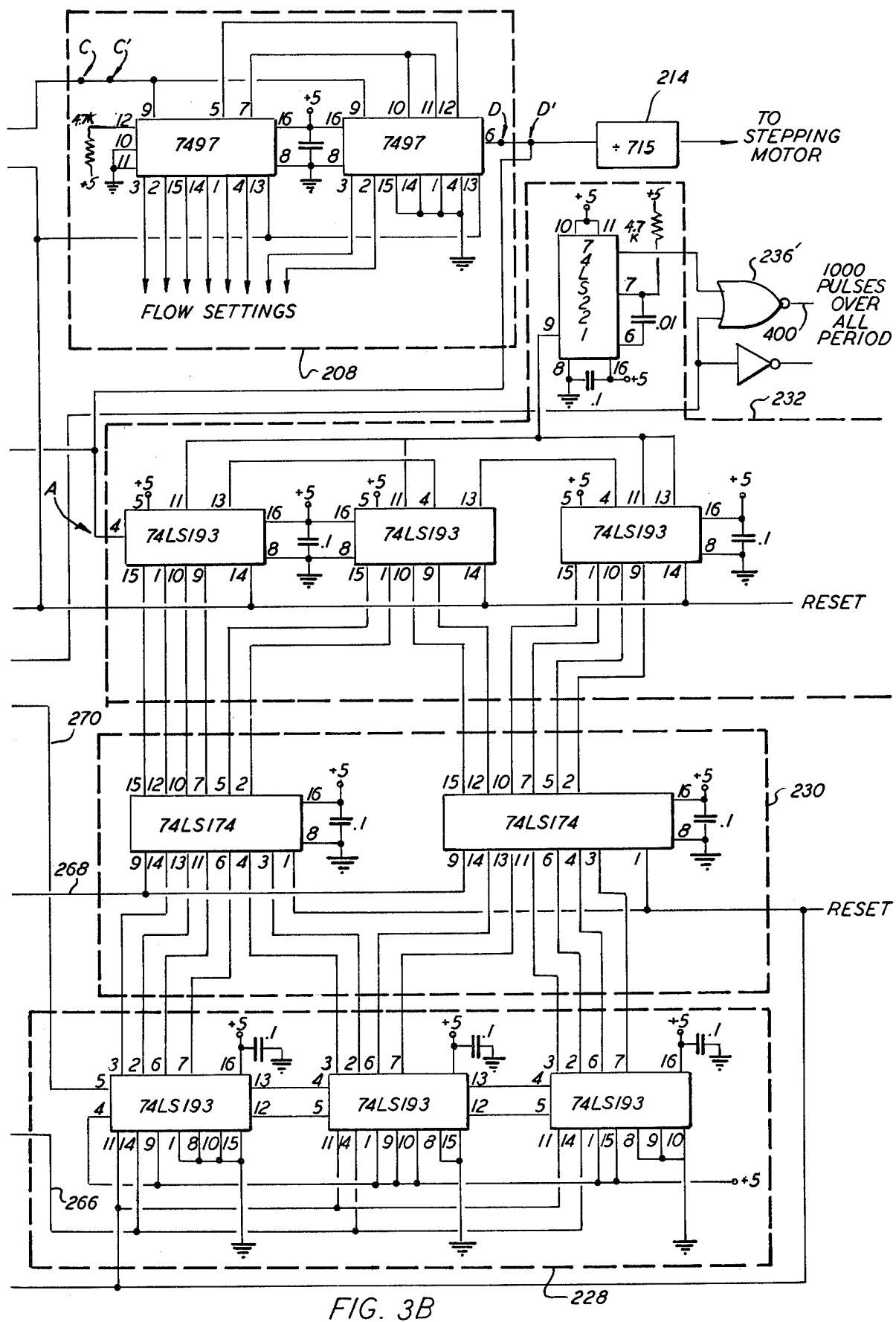

From the discussion above, it is apparent that there is a great deal of interaction between the physical position of the shaft 44 and the operation of the circuitry shown in FIGS. 3A and 3B. It is evident that the position of the interrupter 64 is operative to trigger to the flip-flop 252 so as to stop the transmission of clock pulses through the NAND 222 at the completion of the pumping cycle during which fluid is transmitted from the pump 36 to the column. It has been found that, due to slight variations in size of the pump 36 and its components, as well as other factors, that the interrupter 64 has to be adjustably positioned on the shaft 44 so as to permit the circuitry according to the present invention to operate correctly. Such adjustments typically are made in the manufacturing process of the instrument and, when necessary, adjustments can also be made by trained service technicians. Once the adjustment is properly made, however, the circuit will function accurately.

As an alternative to the mechanical positioning of the interrupter 64, it is possible to provide an electronic circuit for accomplishing the adjustment necessary to make the circuit perform properly. As already indicated, this modification is accomplished by the alternative configuration illustrated in FIG. 2A. This modification is accomplished by modifying the circuitry of FIGS. 3A and 3B in the following manner. The output of the oscillator 200 at point B is disconnected from the scaling circuit 204 and the scaling circuit 204 is disconnected from the flow scaling 208 at point C. In addition, the output of the flow scaling 208 is disconnected at point D from the rest of the circuitry. Thereafter, the oscillator 200 output at B is coupled to the flow scaling circuit 208 at point C', and the flow scaling 208 output at point D is coupled to the input of the scaling circuit 204 at point B'. The output of the scaling 204 at point C is then connected to the remainder of the circuitry at point D'. Then, the circuit of FIG. 4 is coupled into the circuitry of FIGS. 3A and 3B as modified above in the manner shown in FIG. 4. The BCD switches of FIG. 4 are then adjusted by the technician until the circuitry produces 1000 pulses at the output of circuit 236 over the time period during which fluid is introduced into the column by the pump 36.

The output of the gate 236 couples to the valve proportioning circuitry of FIG. 5 via the line 400. The clock pulses appearing on the line 400 are utilized in a manner discussed below to cause the counters 402, 404, 406 and 408 to count down during the pumping cycle, i.e., the time during which the pump 36 is delivering fluid via the pipe 12 to the column.

The counters 402, 404, 406 and 408 are count down counters. One counter useful for this purpose has the commercial designation 74LS193 which can be coupled with other such circuits to provide a single counter such as counter 402.

The counter 402 is coupled to a data source 410 for the count that is to be counted down by the counter 402. One such source 410 could be a digiswitch or the like set to the value desired to be set into the counter 402. It is also possible to couple the counter 402 to a data bus and have a microprocessor gate the desired data into the counter 402. In a similar manner, the counters 404, 406 and 408 are coupled to data sources 412, 414 and 416. As previously mentioned with respect to the data source 410, the sources 412, 414 and 416 each may comprise a digiswitch or a microprocessor, as well as any other suitable source of digital data for gating into the counters 404, 406 and 408.

The counters 402, 404, 406 and 408 each have a gate input designated by the letter G which is coupled to a LOAD line designated as 418. A suitable gating pulse is developed on the LOAD line 418 which gates the data from the data sources 410, 412, 414 and 416 respectively into the counters 402, 404, 406 and 408. The gating of the data into the counters 402, 404, 406 and 408 occurs at a time after the pump 36 stops delivering fluid to the column on one pumping cycle and prior to the time that it starts delivering fluid to the column during the next pumping cycle.

Each of the counters 402, 404, 406 and 408 have a borrow output designated B. Each of these borrow outputs B are at a positive or a high voltage level so long as the counter has a number in it greater than zero. When the counter goes to zero, a borrow indication is developed at the borrow output B which comprises a low level signal. This low level signal is utilized in a manner which will become evident from the following discussion.

The valve clock signal on line 400 is coupled to one input of an AND gate 420 whose output couples to the clock pulse input C of the counter 402. The other input to AND gate 402 couples to the borrow output B from the counter 402. Accordingly, the AND gate 402 is operative to gate pulses from the line 400 to the clock input C of counter 402 so long as the borrow output B of the counter 402 is positive, which will be the case so long as there is a count in the counter which is greater than zero. When the counter 402 goes to zero, however, the borrow output at B goes low and this low signal is coupled to one input to the AND gate 420. Thereafter, clock pulses on the line 400 are inhibited from passing to the counter 402 and hence, the counter 402 remains at a value of zero. The borrow output of the counter 402 is propogated via an EXCLUSIVE OR circuit 422 which, as wired, operates as an inverter. The EXCLUSIVE OR circuit 422 is utilized primarily for manufacturing and test purposes, although it will be recognized by those of skill in the art that an inverter could also be used. The function of the circuit 422 is to make the level on the line 424 high when the counter 402 is at a value of zero.

The line 424 comprises one input to a second AND gate 426 whose output couples to the clock input to the B counter 404. The clock pulses on the line 400 also couple to another input to the AND gate 426. The remaining input to the AND gate 426 couples to the borrow output of the counter 404. Accordingly, clock pulses appearing on the line 400 are gated to the clock input to the counter 404 whenever the counter 402 is zero and the counter 404 is not zero. The counter 404 will continue to count down until it reaches a value of zero whereat the borrow output goes low. This borrow output going low is coupled via the line 428 to one input to AND gate 426 thereby inhibiting further clock pulses from being coupled thereby to the clock input C of the counter 404. The signal on the line 428 is inverted by the exclusive OR circuit 430, which is wired as an inverter and coupled to one input of AND gate 432. A second input to the AND gate 432 is the line 400. A third input to the AND gate 432 is the line 434 which is high whenever counter 402 is zero. Accordingly, the AND gate 432 passes the clock pulses on line 400 to the clock input C of counter C 406 whenever counter 402 and counter 404 are zero and counter 406 is not zero. Once the counter 406 goes to zero, the line 436 goes LOW, thereby inhibiting the AND gate 432 from passing pulses to the clock input to the counter 406.

The line 436 couples to an EXCLUSIVE OR circuit 438, which is wired as an inverter, whose output is coupled to one input of another AND gate 440. The line 434 couples to another input of the AND gate 440. A line 444 from the output of the exclusive OR 430 couples to yet another input to the AND gate 440. In addition, the borrow output 446 from the counter 408 couples to an input of the gate 440 as does the line 400. Accordingly, the gate 440 whose output is coupled to the clock input to the counter 408 is operative to apply clock pulses to the counter 408 whenever the counter 402, the counter 404 and the counter 406 are each zero and the counter 403 is not zero. As soon as the counter 408 counts down to zero, however, the line 406 goes low and further clock pulses on the line 400 are inhibited from passing to the clock input of the counter 408 by the AND gate 440. Accordingly, the circuitry just described with respect to FIG. 5 is operative to count down each of the counters 402, 404, 406 and 408 in that order.

The counters 402, 404, 406 and 408 of FIG. 5 control the solvent valves illustrated in FIG. 1 in accordance with the truth table of FIG. 5A. The value for X and Y is the binary value of the data which is set into the latch 450 from a data source 452 which may comprise digiswitches, or, alternatively, may comprise a microprocessor or any other source of selection data for selecting the four possible values which can be loaded into the latch 450. When the latch 450 is set so that the values of X and Y are both zero, then the counter A (402) is used to control the time that valve A is open, counter B (404) is used to control the time valve B is open, counter C (406) is used to control the time that valve C is open and counter D (408) is used to control the time that valve D is opened. When other data combinations are in the latch 450, different valves are controlled by the counters in accordance with the truth table of FIG. 5A.

It should be noted that the valve controlled by the counter A remains open, except during the time when the valves controlled by counters B, C and D are open. This is illustrated in FIG. 6, which is a timing chart for the valve control signals, assuming that the latch 450 has a binary 00 in it.

It has been found advantageous to have the counter A control the valve for the solvent which has the largest percentage in the overall solvent mix being entered into the column. Accordingly, it is important for the operator or the microprocessor to make sure that the value loaded into the latch 450 corresponds to 00 if the solvent controlled by valve A is the majority, the value is 01 if the solvent controlled by valve D is the majority, the value is 10 if the solvent controlled by valve C is the majority and the value is 11 if the solvent controlled by valve B is the majority.

The circuitry of FIG. 5 accomplishes this value reduction via a number of elements. The borrow output of counter 402 is coupled via a line 454 to an OR gate 456 whose output is coupled to the (a) input to the four to one line selector 458. Accordingly, whenever the counter 402 is not zero, the (a) input to the four to one line selector 458 is a one or high. This will be the case between the time counter 402 is loaded until it has counted down to zero. Accordingly, by reason of the operation of the four to one line selector 458, the valve A, if the data in latch 450 is 00, is open and valve B, C and D are closed. Valve A is again opened after valves B, C and D have been opened and closed for the period of time specified by the counters 404, 406 and 408. This is accomplished by the AND gate 460, which has four inputs, each of which goes high when the counter coupled thereto goes to zero. For example, the line 424 couples to the input of AND gate 460 and this line goes high when the counter 402 goes to zero. The line 462 also couples to the AND gate 460 and this line goes to a value of one or high when the counter 404 goes to zero. The line 464 couples to another input of AND gate 460 and this line goes high or to a value of one whenever the counter 406 goes to zero. The line 466 couples to the output of an exclusive OR circuit 468 which is wired as an inverter. Whenever the borrow output on line 446 goes low, the EXCLUSIVE OR circuit 468 inverts it and places a high level signal on line 466 which couples to the input of the AND gate 460. When all the inputs to the gate 460 are high, the output goes high and this high level signal is transmitted by the OR gate 456 to the a input to the four to one line selector 458. In this manner, in accordance with the truth table of FIG. 5A, the valve controlled by counter A is again opened, once the counters A, B, C and D go to zero.

As noted earlier, when counter A goes to zero, counter B begins to count, and when the value in latch 450 is 00, counter B controls valve B. This is accomplished by way of the AND gate 470, which has one input coupled to line 424 and its other input coupled to line 428. Accordingly, when counter B is not zero, line 428 is high and when counter A is zero, line 424 is high. This condition indicates that counter B is counting down and accordingly, the AND gate 470 applies a high or a one signal to the b input to the four to one line selector 458.

Once counter B goes to zero, the output of the AND gate 470 goes low because the signal on line 428 at its input goes low. At this point, AND gate 472 takes over. This AND gate 472 has one input coupled to line 462, a second input coupled to line 434 and a third input coupled to line 456. Line 462 is high when the counter B goes to zero. The line 434 goes high when the counter A goes to zero and the line 436 is high so long as the counter C is not zero. Accordingly, the AND gate 472 applies a one signal to the c input to the four to one line selector 458 when counter A and counter B are both zero and counter C is not zero. Once counter C goes to zero, the line 436 goes low and the output of AND gate 472 also goes low. However, AND gate 474 takes over controlling the d input to the four to one line selector 458. The AND gate 454 has an input coupled to line 434 which goes high when counter A is zero. It also has an input coupled to line 462 which goes high when counter B is zero. The remaining input is coupled to line 464 which goes high when counter C is zero. Accordingly, the output of AND gate 474 is only high when counters A, B and C are zero and counter D, which is also coupled to the input of AND gate 474, is not zero. Once the counter D goes to zero, however, the output on line 446 goes low and, therefore, the output of AND gate 474 goes low. This condition, as indicated earlier, actuates AND gate 460 to thereby cause the (a) input to the four to one line selector 458 to go high thereby reopening valve A if 00 is in latch 450.

In the operation of the circuitry of the present invention in controlling the valves which control solvent delivery to the pump mechanism of FIG. 1, it has been found to be advantageous to have the majority solvent introduced into the pump 28 both at the beginning and before the end of the pumping cycle with the other valves being opened and closed between the time that the valve for the majority solvent is open. Therefore, when the counter A is set prior to the beginning of the pumping cycle, it is convenient to set the counter A to a value representative of one-half of the time that the solvent A is to be introduced into the pump 28. This is easily accomplished by having the data source 410 set to one-half the value desired, and in the case of a digiswitch, it is simply a matter of setting the switch accordingly. In the case where the data source 410 is a microprocessor, however, this function is very easily accomplished by simply loading the data into the counter 402 shifted right by one bit position which, in effect, divides the input number by two.

The four to one line selector 458 and the latch 450 shown in FIG. 5 are easily implemented by off-the-shelf hardware in the manner indicated in FIG. 7. In particular, the latch 450 may comprise a circuit type having the standard commercial designation 74LS175. The four to one line selector 458 may be made by coupling two circuits having circuit designation 74LS153 in the manner illustrated in FIG. 7. The latch 450 is loaded by the inverse of the LOAD signal applied on line 418 of FIG. 5.

In the operation of the circuitry of FIG. 5, as indicated above, the latch 450 is set in a manner so as to determine the valves which are controlled by which counters 402, 404, 406 or 408. Once that determination has been made, then the counters must be set to a value that corresponds to the percentage of the particular solvent controlled by that counter that is desired to be placed into the column of the liquid chromatograph. In addition, it will be remembered that the valve clock line 400 has 1000 pulses on it during the time period that solvents are introduced into the pump 28. Accordingly, if, for example, the valve controlled by counter B is to introduce a solvent that is to comprise 20 percent of the fluid in the pump 28, then the counter B must be set to 200, which comprises 20 percent of the pulses developed on the line 400 during the time that the pump 28 is filled. If, for example, the solvent control valve that is controlled by counter C is to introduce that solvent so it will be 17 percent of the composition of the fluid in the pump 28, then the counter C must be set to 170. If the counter D is to control the introduction of a solvent in a percentage of, for example, 3 percent, then the counter D must be set to a value of 30. The remaining percentage is allocated to the majority solvent, which, for the example being developed, is 60 percent. Since, as already indicated, it is advantageous to set the counter A to one-half the desired value, a count of 300 is set into counter A. Accordingly, once the pumping cycle begins and pulses start appearing on the valve clock line 400, the valve controlled by counter A, which previously was open prior to filling pump 28, will remain open for a count of 300 pulses when counter A goes to zero. Then, counter B takes over control and will open a different valve for the time it takes for 200 pulses to appear on line 400. Thereafter, counter C takes over control of another valve which remains open for the time period it takes for 170 pulses to occur on the line 400. Finally, counter D takes over control and the valve control thereby will remain open for a period of time that it takes for 30 pulses to appear on line 400. Thereafter, the AND gate 460 takes over control as all the counters are now zero and the majority solvent valve which was previously controlled by the counter 402 is again opened. Since the counters A, B, C and D have previously controlled valves coupled thereto for the time it has taken to produce 700 pulses on the clock line 400, 300 clock pulses remain during the pumping cycle. Accordingly, an additional fluid in the amount of 30 percent of the total amount in the pump 28 will be introduced into the pump 28 through the valve previously controlled by counter A before the end of the pumping cycle.

While the foregoing description and drawings have described certain circuit components with particular emphasis on their assigned parameter value or standard commercial designation, this has been done purely for clarity and reader convenience and is not intended as a limitation on component value or type or as a restriction on the scope of the invention. This will be clear to those of ordinary skill in the art as numerous circuit type substitution types are available. The invention is, therefore, only intended to be limited by the appended claims or their equivalents.

What is claimed is:

1. A circuit for producing a plurality of control signals comprising:
   means for producing a selected number of pulses during a given time period;
   a plurality of counters each settable to a given value prior to the start of said time period, the sum of the values set into said counters being less than or equal in number of said selectable number of pulses;
   means to selectively apply said pulses to one of said counters at a time to cause that counter to count down to zero and thereafter apply pulses to another said counter causing it to count down, said selective pulse applying means being operative to count all said counters to zero during said given period in a prescribed sequence;
   means responsive to all but one of said counters as each said counter is counted down to produce a unique control signal indicative of a particular one of said counters being counted down; and
   means responsive to said one remaining counter to produce another unique control signal whenever said one counter is not zero or when all said counters are zero.

2. The circuit of claim 1 wherein said selected number of pulses is a power of 10.

3. The circuit of claim 1 wherein said selected number of pulses is 1000.

4. The circuit of claim 1 wherein each said counter is a count down counter including an output signal indicative of the fact that value stored therein is not zero.

5. The circuit of claim 1 wherein said means for producing a selected number of pulses includes:
   a first pulse counter responsive to pulses at one rate for counting them during said time period;
   means to store the count of said first said pulse counter during the next cycle; and
   a second pulse counter means responsive to pulses at a second rate greater than said first rate and for producing a pulse at its output for every N pulses at said second rate where N is the number stored in said means to store.

6. The circuit of claim 1 wherein each control signal is coupled to a valve for controlling the flow of fluid therethrough.

7. A circuit for dividing a time period, which is gradually changeable in length, into a fixed number of subintervals comprising, in combination:
   means defining the time period to be subdivided;
   a source of pulses at a first pulse rate;
   means responsive to said source of pulses to produce pulses at a second pulse rate which is equal to said first pulse rate divided by M;
   first counter means responsive to said pulses at said second pulse rate and also responsive to said means defining a time period to be subdivided, said first counter means being operative to count the number of pulses at said second pulse rate occurring during said time period to be subdivided;
   latch means to store the count stored in said first counter means at the conclusion of a time period;
   a second counter means, responsive to said latch and to said pulses at said first pulse rate during the next time period to produce a pulse at its output for every N pulses input thereto at said first rate where N is the number stored in said latch means, said second counter producing M pulses at its output during the period to be subdivided.

8. The circuit of claim 7 additionally including first scaling means to adjust the rate of said first pulse rate.

9. The circuit of claim 7 or 8 additionally including second scaling means to adjust the rate of said pulses applied to said second counter means independently of said first pulse rate.

10. The circuit of claim 7 wherein M is a power of 10.

11. The circuit of claim 8 wherein M is 1000.

12. The circuit of claim 1 wherein said means defining said time period to be subdivided includes a second latch which is set at the beginning of said period to be subdivided and reset at the end of said period to be subdivided.

13. A circuit for dividing each of a plurality of repeating time periods into a plurality of subintervals, each such time period being a length which may be different from either the preceding or succeeding time period, comprising, in combination:
   means producing a start indication and a stop indication at the beginning and the end of each said repeating time period;
   an oscillator producing pulses at a frequency $f_0$;
   at least one scaling circuit responsive to said oscillator to procduce pulses at a rate of $Nf_0$ where N is a number between 0 and 1; ;
   means responsive to said scaling circuit to produce pulses at a frequency of $Nf_0/M$;
   first counter means for counting said pulses at a frequency of $Nf_0/M$ occurring between each said start indication and the follwoing stop indication, the count so derived being designated P;
   means to store the count P after each successive stop indication;
   second counter means responsive to said pulses at a frequency of $Nf_0$ and to the count P in said means to store the count P to produce a pulse at its output each time said second pulse counter has counted P pulses at frequency $Nf_0$.

14. The circuit of claim 13 additionally including a further scaling circuit for scaling the frequency of pulses counted by said second counter.

15. The circuit of claim 13 where M is a power of 10.

16. The circuit of claim 13 where M is 1000.

17. A circuit for dividing a time period, which is gradually changeable in length from one period to the next, into a fixed number of subintervals comprising, in combination:
   a first source of pulses;
   a control signal which is active between the beginning and the end of a period to be divided into a plurality of parts, said control signal being characterized in that the active state between the beginning and the end of said period is variable in time from one period to the next;
   a first counter circuit responsive to said pulses and to said control signal to count said pulses while said control signal is active;
   a latch circuit to store the content of said first counter during the time between the end of one period and the beginning of the next period, the stored count being designated N;
   means to reset said first counter after said latch is filled and before the beginning of said next period;
   a second source of pulses;
   a second counter responsive to said count N in said latch and to said second source of pulses to produce an output pulse for every N pulses from said second source of pulses.

18. The circuit of claim 17 wherein the frequency of said second source of pulses is substantially M times the frequency of said first source.

19. The circuit of claim 18 where M is a power of 10.

20. The circuit of claim 18 where M is 1000.

21. A circuit for producing a plurality of control signals for a selectable percentage of a time period during which a known number of clock pulses occur, the circuit comprising, in combination:
   n counters where n is an integer, each said counter being settable and, in response to clock pulses applied to its clock input, each said counter will count down;
   means coupled to each said counter to set each counter to a selectable value prior to the time period when said clock pulses occur;
   means to apply the clock pulses to only one said counter at a time until it counts to zero whereat the clock pulses are applied to another said n counter;
   means responsive to each said counter when it is being counted down to produce a unique control signal for controlling a device coupled thereto; and
   means to actuate a selected one of said control signals whenever all said counters are zero or when one selected counter is not zero.

22. The circuit of claim 21 additionally including means to select which said unique control signal is actuated when a given counter is counted down.

23. The circuit of claim 21 or 22 wherein said selected counter is set to a value less than the number of pulse counts desired to occur while said selected control signal is actuated.

24. The circuit of claim 21 or 22 wherein said selected counter is set to a value of one half the number of pulse counts desired to occur while said selected control signal is actuated.

* * * * *